United States Patent [19]

Hirsch et al.

[11] 4,202,353
[45] May 13, 1980

[54] TEMPERATURE AND RESPIRATION SENSING PROBE

[75] Inventors: Leon C. Hirsch, Westport; Paul O. Rawson, Easton; Louis E. Nagy, Killingworth, all of Conn.

[73] Assignee: United States Surgical Corporation, Stamford, Conn.

[21] Appl. No.: 17,098

[22] Filed: Mar. 5, 1979

Related U.S. Application Data

[63] Continuation of Ser. No. 771,012, Feb. 22, 1977, abandoned.

[51] Int. Cl.$^2$ .............................................. A61B 5/00
[52] U.S. Cl. .................................... 128/724; 128/736
[58] Field of Search ............... 128/670, 671, 724–725, 128/736; 73/339 R, 343 R, 343 B, 344, 362 R, 362 AR, 374

[56] References Cited

U.S. PATENT DOCUMENTS

| | | | |
|---|---|---|---|
| 3,426,745 | 2/1969 | Farr | 128/730 |
| 3,477,292 | 11/1969 | Thornton | 73/362 AR |
| 3,645,133 | 2/1972 | Simeth et al. | 73/204 |
| 3,880,591 | 4/1975 | Burroughs | 128/716 |
| 3,884,219 | 5/1975 | Richardson et al. | 128/736 |
| 3,903,742 | 9/1975 | Colton | 73/194 B |
| 3,949,737 | 4/1974 | Nielsen | 128/726 |
| 3,999,537 | 12/1976 | Noiles | 128/736 |
| 4,036,211 | 7/1977 | Veth et al. | 128/736 |

Primary Examiner—Robert W. Michell
Assistant Examiner—Francis J. Jaworski
Attorney, Agent, or Firm—Fleit & Jacobson

[57] ABSTRACT

A temperature and respiration sensing probe which eliminates any problems associated with orientation in relation to either a hygenic cover or insertion into the patient's mouth. A means for sensing air movements caused by exhaled respiration is located and entirely housed inside the probe body and is caused to be in communication with the respiration by means of a large inlet aperture, which extends in a transverse direction through the entire probe body. One of the two inlet openings so formed is covered by the sheath. Exhaust ports are provided along the narrow edges of the rear of the probe body such that in using the probe, the operator's fingers will not occlude or obstruct the exhaust.

8 Claims, 14 Drawing Figures

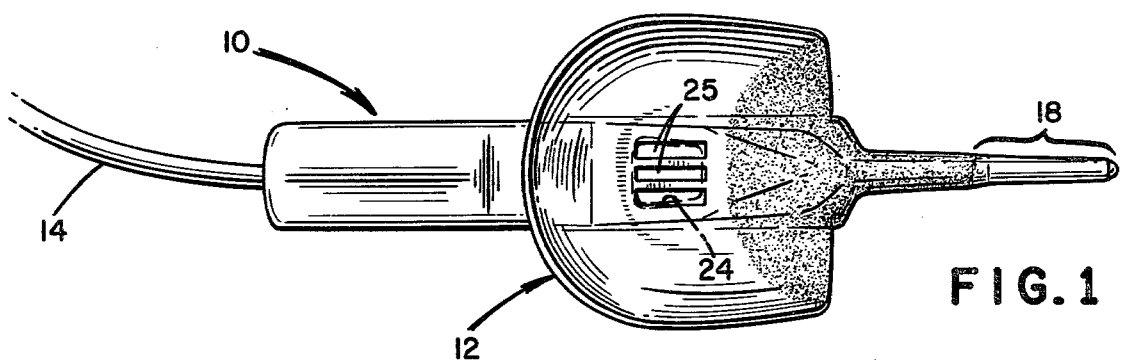
FIG. 1
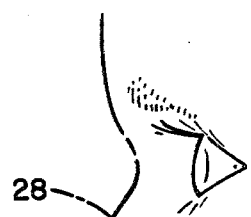
FIG. 3
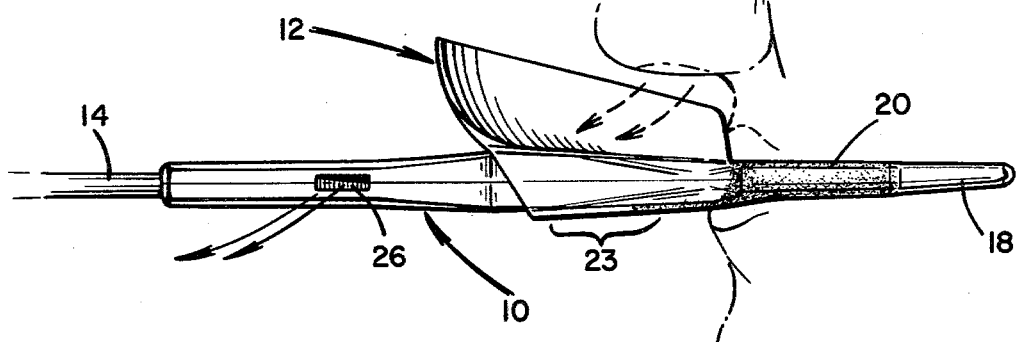
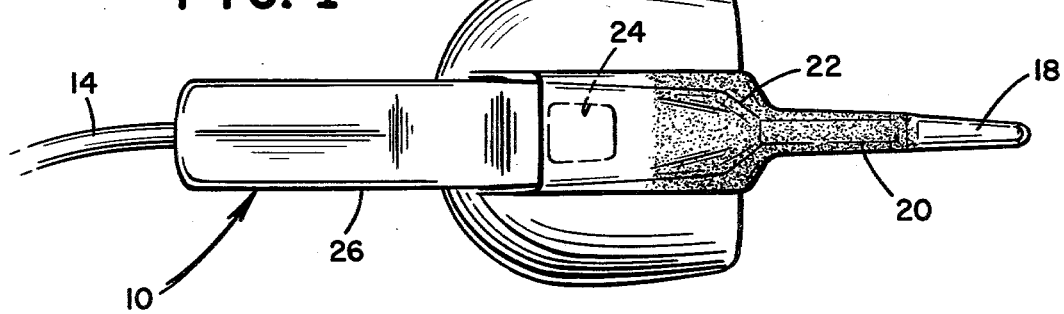
FIG. 4
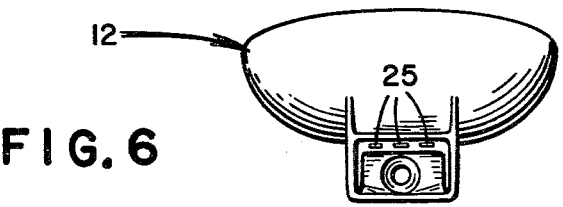
FIG. 6

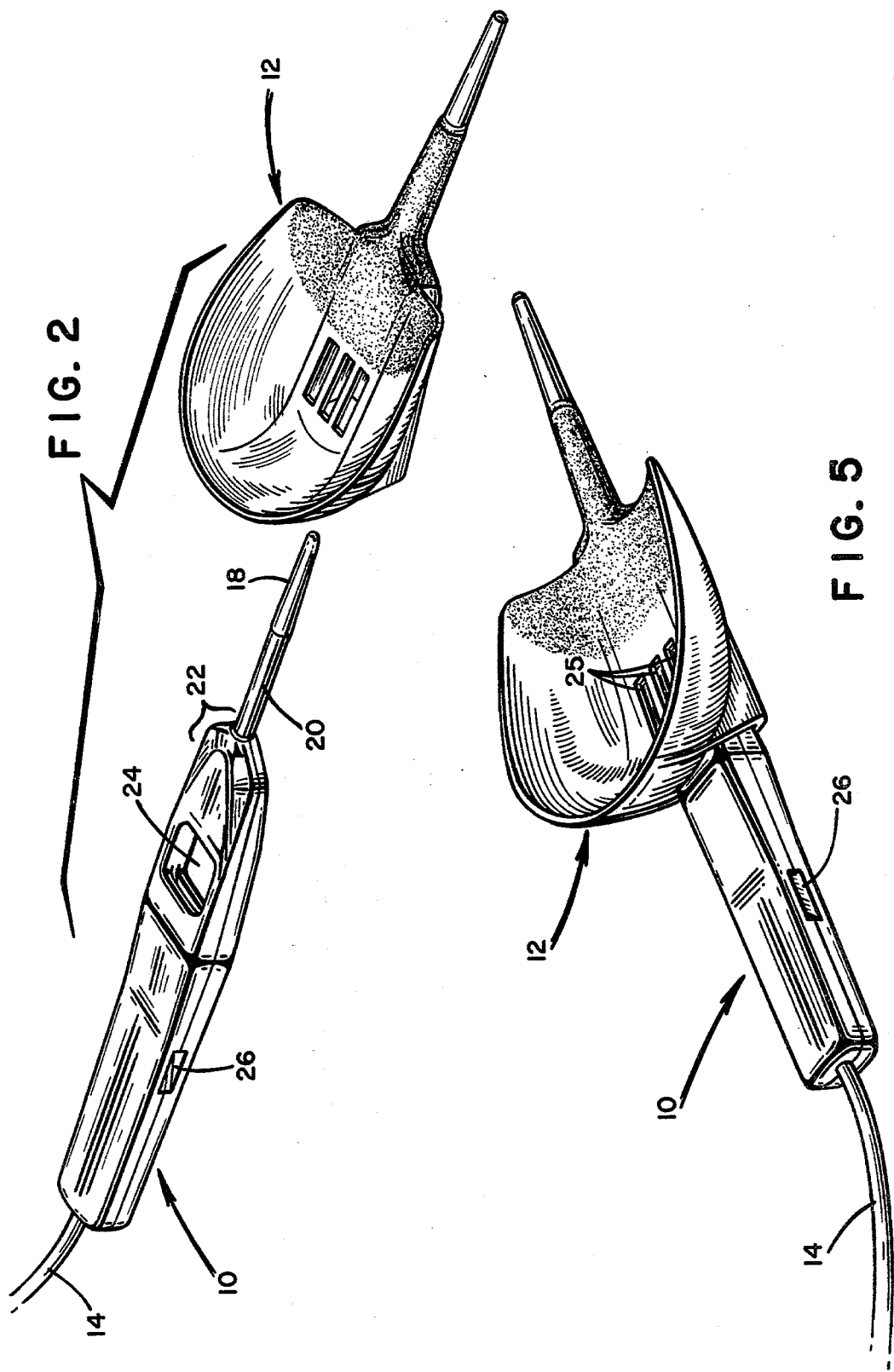

TEMPERATURE AND RESPIRATION SENSING PROBE

This is a continuation of application Ser. No. 771,012, filed Feb. 22, 1977, now abandoned.

BACKGROUND OF THE INVENTION

The present invention relates to a probe apparatus for insertion in a patient's mouth and which contains electrical devices for sensing both the patient's temperature and respiration rate.

Due to the recent upsurge in the use of electrical/electronic measuring systems in lieu of the classic means used for sensing various patient vital signs, a need has risen for a simple but efficient sensing probe which may be used repeatedly by a succession of patients. In the past, it has been known to use a combination of sensors each intended to sense a different physiological parameter and all being contained within the same housing. For example, it is known to utilize a temperature sensor, respiration rate sensor and pulse rate sensor all contained within the same housing and which provide the appropriate analog signals to an instrument by the use of suitable connecting cables. The heart of the majority of past temperature and respiration rate sensor systems has been a thermistor which, as is well known, presents a varying electrical resistance in response to variations in temperature. Thermistors have been utilized in the past to provide an indication of the patient's temperature by locating a thermistor in the end of a rod or tube and placing the tube under the patient's tongue. Of course, such thermistor probes may also be used to take the patient's temperature rectally. Similarly, because a person's respiration causes air movement, it is known to detect such air movement by placing a thermistor in the air stream. It is known to heat the thermistor to approximately 50 or 75 degrees Fahrenheit above ambient in still air. Then air motion due to respiration, including the passage of warm expired air, will cool the thermistor, thereby causing cyclic resistance changes coincident with the rate of exhalation. Systems have been disclosed wherein a thermistor is actually located within the nasal passages of a patient. However, more recently temperature sensing probes have been disclosed with a first thermistor located on one end of a rod for insertion into the patient's mouth, and a second thermistor located on the surface of the probe, such that the exhalation from the patient's nose passes over the thermistor and thereby provides the necessary temperature variations. These temperature variations are subsequently used to calculate the respiration rate.

Although such sensing probes have been disclosed and used in the past, they have all been beset by various problems, not the least of which is a bulky design, thereby making it difficult for a patient to comfortably retain the probe in his mouth. Problems have also been found in that when placing a cover over the probe, the operator must use extreme care so as to properly seat the cover on the probe and, more importantly, to properly orient the cover in the patient's mouth so that the respiration sensor is not obstructed or misaligned. A further problem in prior respiration sensing probes has been in locating the thermistor exterior to the housing. In this respect, various designs have been utilized wherein the respiration sensing thermistor sits on a small stalk located midway on the probe body so that the patient's exhalations pass over the thermistor. This design is not only cumbersome but is also vulnerable to damage by rough handling by the operator.

SUMMARY OF THE INVENTION

It is therefore an object of the present invention to provide a temperature and respiration rate sensing probe which is contained in a single easily handled housing.

It is another object of the present invention to provide a sensor probe which utilizes thermistors which are located in such a way as to preclude damage thereto.

It is a further object of the present invention to provide a temperature and respiration rate sensing probe which has a fool-proof configuration in relation to the installation of probe cover, as well as in relation to insertion in the patient's mouth.

It is a still further object of the present invention to provide a patient physiological parameter sensor probe which is not readily susceptable to damage either by the operator or the patient, and which cannot easily be mishandled so as to adversely affect the parameters being measured.

The present invention provides apparatus to achieve these and other objects. The preferred embodiment is disclosed as a thin, streamlined, sensing probe which utilizes a first thermistor located at the end of a non-rigid stalk for insertion under the patient's tongue and which utilizes a second thermistor located within the probe body to measure the patient's respiration rate and which is intended for use with a suitable hygenic probe sheath. The respiration sensing thermistor is located inside the probe housing and is placed in communication with the patient's exhalations by the use of a relatively large inlet aperture located in the probe housing. The present invention provides a fool-proof probe in relation to inserting the probe in a sheath, in that this inlet aperture extends transversely through the entire body of the sensing probe. There is no up or down orientation in relation to the rather flat surfaces of the probe. The operator is only required to firmly insert the probe in the sheath and no other special orientation or turning of the probe or cover is required. The thermistor then communicates with the transverse inlet aperture by a suitable channel which provides a sort of wind tunnel to cause the exhalations to pass over the sensing thermistor. Another feature of the present invention is that the respiration exhaust ports are located on both sides of the probe housing and specifically on the narrow thinner surfaces where an operator or patient is unlikely to grasp the probe and stop the exit air flow and adversely affect the respiration rate being sensed.

The probe of the present invention is also provided with tapered surfaces at the temperature sensing end and also at the leading edges of the housing so that in the first instance the temperature sensor can be forced into intimate contact with the sheath and in the second instance that the probe housing may be guided easily into the awaiting receptacle portion of the sheath.

The above objects as well as other objects will be more clearly explained in relation to the description of the preferred embodiment which follows below.

BRIEF DESCRIPTION OF THE DRAWINGS

FIG. 1 is a plan view from the top of a sensing probe according to the present invention located within a suitable sterile sheath.

FIG. 2 is an exploded perspective view of the sensing probe aligned with, but withdrawn from, the sterile sheath.

FIG. 3 is an elevation view of the sensing probe inserted in the sheath and showing the face of a typical patient in phantom.

FIG. 4 is a view from the bottom of the sensing probe inserted in the sheath.

FIG. 5 is a perspective view taken from the rear of the sensor probe and the sheath combination.

FIG. 6 is an elevation view taken from the rear of the sterile sheath.

DETAILED DESCRIPTION OF THE PREFERRED EMBODIMENT

Figure 7:
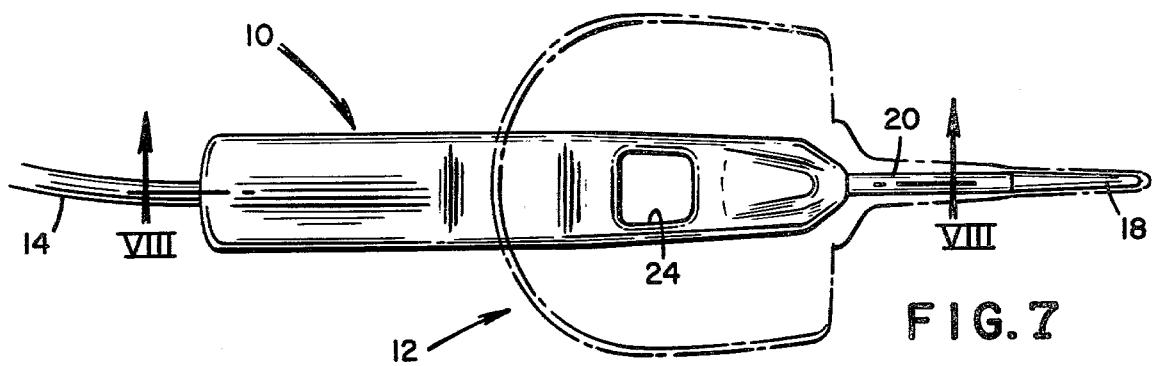
FIG. 7 is a view of the sensing probe and showing the sheath in phantom.

Referring now to FIGS. 1, 3, and 5, the probe body 10 is shown inserted in the unitary hygienic sheath 12. The analog electrical signals sensed by the thermistors located inside the probe 10 are fed to a suitable calculating device by a cable 14. The respiration sensing thermistor is located inside the probe housing 10 while the temperature sensing thermistor is located inside the tip of a metallic cap 18 which is attached to a non-rigid rod 20. Referring now to FIG. 2, the probe 10 is shown outside the sterile sheath 12 but still in axial alignment therewith. The cap 18 is metallic and the non-rigid rod 20 may be nylon or some other plastic. The rod 20 is tubular so that the electrical conductors from the thermistor located in the metal cap 18, may pass therethrough to the body of the probe 10 and ultimately to the cable 14. Generally at 22, the forward tapered portion of the probe body permits easy insertion into and alignment with the sheath 12. Also shown in FIG. 2 is the relatively large inlet aperture 24 which communicates with both of the large flat surfaces of the probe housing 10. Shown at the rear portion of the probe housing 10 is one of the two opposed exhaust ports 26. As will be discussed, the exhalations of the patient are introduced into the inlet port 24 and caused to flow over the thermistor located inside the probe housing and ultimately caused to exit through the two opposing exhaust ports, shown typically at 26.

Referring now to FIG. 3, the probe is shown inserted in the mouth of a patient shown at 28. The operation of the probe may be seen more clearly in this view, in that the metallic cap 18 which is covered by the sheath is located in the patient's mouth and under the patient's tongue in order to properly sense the body temperature. Simultaneously, with sensing such temperature, exhalations from the patient's nose which will be the entire exhalation of the patient since he is required to have his mouth closed, will be directed toward the inlet aperture 24 of the probe and a portion of same will exit through the exhaust ports 26. For proper function, it is important that the lower opening of the aperture 24 be closed to cause an adequate fraction of the exhalations to pass into the probe housing. To that end, the bottom of the sheath is a solid portion so that the exhalations do not simply flow through aperture 24, which, as provided by the present invention, extends completely through the probe housing in a transverse direction. As discussed above, the probe housing is provided with an inlet aperture which is open from both sides and this construction provides a fool-proof probe which does not require a top or bottom orientation of the probe on the part of the person inserting the probe into a sheath. The sheath may be made of a clear or translucent plastic such as polypropylene or polyethylene. Accordingly, the probe may be seen inside the sheath itself as in FIG. 4.

In FIG. 4, the metallic cap 18 housing the temperature sensing thermistor is shown conical with a blunt point. This shape facilitates a snug fit with the sheath. FIG. 4 also shows more clearly the manner in which the leading end of the probe housing is tapered at 22 in order to be guided more easily into the receiving portion of the sheath.

FIG. 5, shows the probe housing 10 inserted in a sheath 12, the entry of cable 14 into probe 10, one of the two exhaust ports 26, and the openings 25 in the sheath 12 which communicate with aperture 24.

FIG. 6 shows a rear view of the sterile sheath 12 showing the portion of the sheath which receives the probe of the present invention.

FIG. 7 shows the probe provided by the present invention with the sheath seen in phantom. In this view, it may also be seen that the metallic tip 18 is tapered and that the inlet port 24 extends transversely through the entire probe housing.

Figure 8:
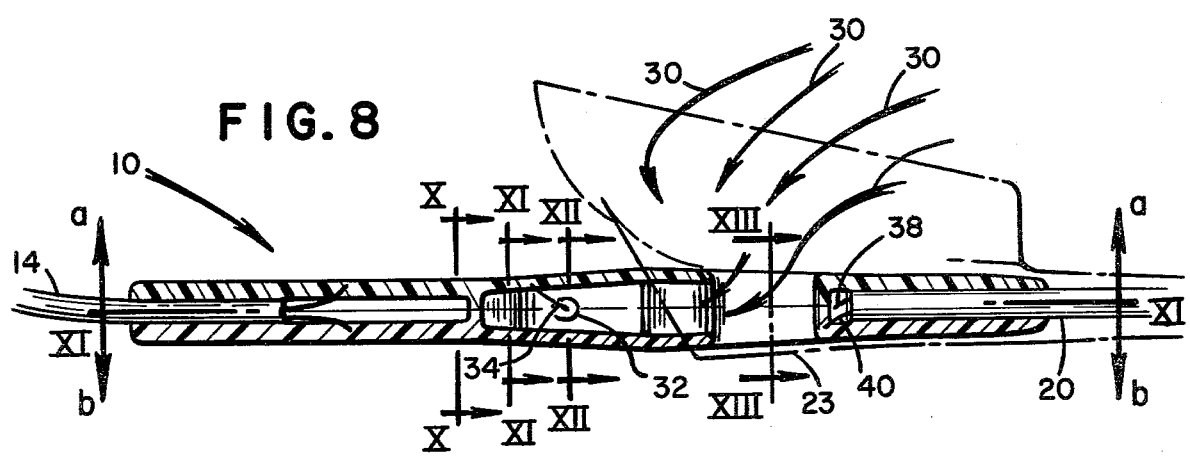
FIG. 8 is a longitudinal sectional view of the sensing probe of FIG. 7 taken along section line VIII.

FIG. 8 shows the non-rigid nylon tube 20, the flexible cable 14, and the manner in which the exhalations, shown generally by the arrows at 30, are conducted into the body of the probe housing. The sheath 12 shown in phantom is provided with lower surface 23 which covers the lower opening of aperture 24. The velocity of exhaled air stream 30, blocked by surface 23, is converted to a stagnation pressure within aperture 24. This stagnation pressure forces part of the exhaled air into and through channel 44, and to thereby flow past thermistor 32, ultimately to exit at ports 26. Associated with the thermistor are electrical conductors 34 and 36, which exit via cable 14. Also shown in the sectional view of FIG. 8 are the electrical connection leads 38 and 40 from the temperature sensing thermistor in the metallic cap.

Figure 9:
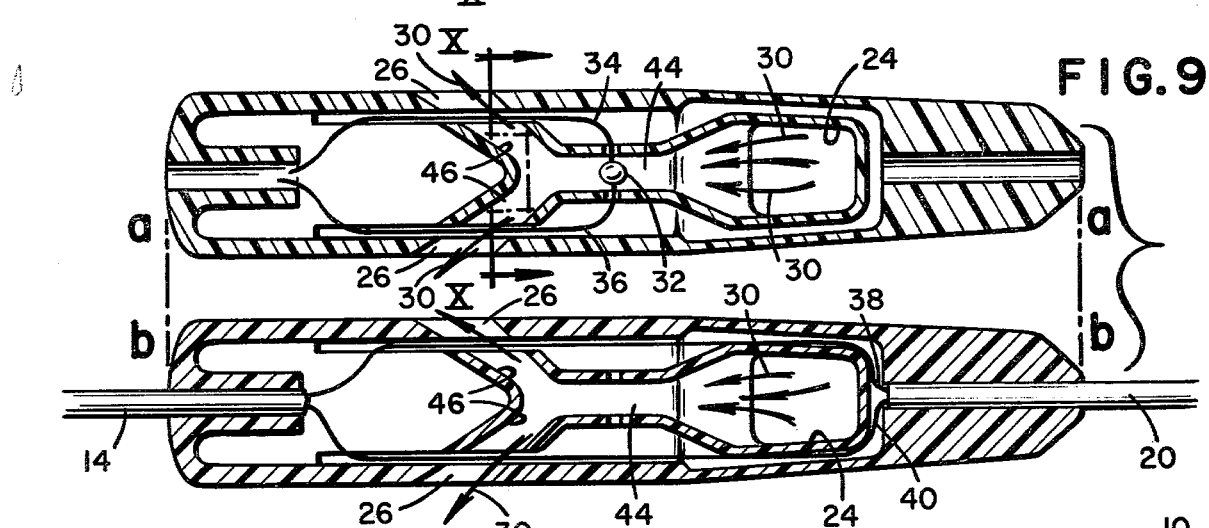
FIG. 9a is a section of the bottom half of the sensing probe taken along section line IXa.
FIG. 9b is a section of the top portion of the probe taken along section line IXb.

Referring now to FIG. 9A, the relatively large inlet aperture 24 communicates with channel 44 thereby directing the exhaled air 30 past the thermistor 32. Change in motion of air past thermistor 32 causes resistance variations in synchronization with exhalations. The longitudinal channel 44 is provided to permit air to freely flow over the thermistor 32 before being exhausted at ports 26. This longitudinal channel 44 then branches into a Y-shaped conduit shown generally at 46. The branches 46 terminate at exhaust ports 26. FIG. 9b also shows that the inlet aperture 24 is in communication with the exhaust ports 26 by means of the longitudinal channel 44 and the Y-shaped branches 46. Also shown in FIG. 9b are leads 38 and 40 from the temperature sensing thermistor (not shown) located in the metallic cap 18. These wires 38 and 40 are routed through suitable channels located along the longitudinal edges of the probe housing 10.

Figures 10, 11:
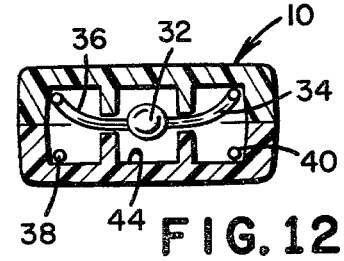
FIG. 10 is a transverse cross-section of the temperature and respiration sensing probe of FIG. 8 taken along line X and showing the exit or exhaust ports for the respiration exhalation.
FIG. 11 is a transverse cross-section of the temperature and respiration sensing probe of FIG. 8 taken along line XI and showing the manner in which the electrical connections to the thermistor sensors are arranged inside the probe housing.

In FIG. 10 the channel 44 and branches 46 are shown. Also shown in this transverse section are the four electrical connectors 34, 36, 38 and 40 which exit the housing by cable 14.

FIG. 11 shows a transverse section similar to that of FIG. 10; however, it is now taken at a location closer to the front of the probe, and shows the longitudinal channel 44 through which the exhalation is intended to pass.

Figure 12:
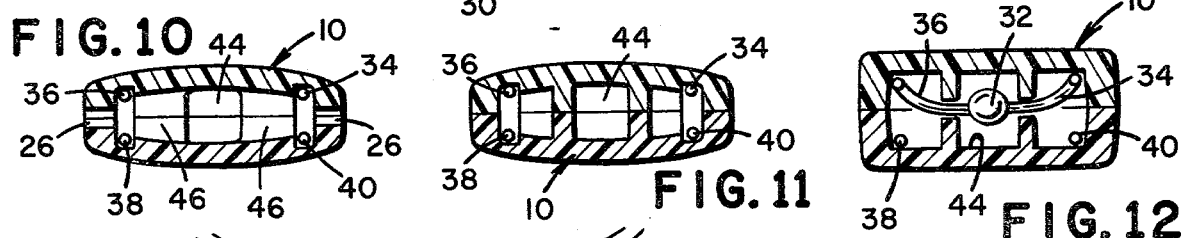
FIG. 12 is a transverse cross-section of the temperature and respiration sensing probe of FIG. 8 taken along section line XII and showing the manner in which the respiration rate sensing thermistor is affixed within the sensing probe housing.

FIG. 12 shows the location of the thermistor 32 which is used to sense temperature fluctuations caused by the exhalations of the patient. The thermistor 32 is supported by leads 34 and 36, clamped by the opposing parts of the housing 10, and is located in the longitudinal channel 44.

Figure 13:
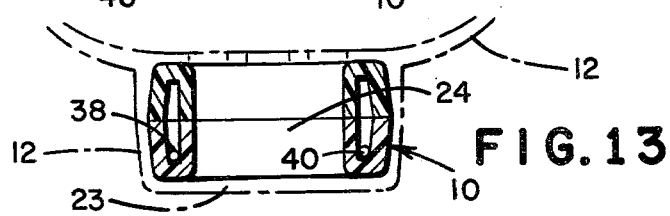
FIG. 13 is a transverse cross-section of the temperature and respiration sensing probe of FIG. 8 taken along line XIII and showing the manner in which the transverse inlet port is arranged in the probe housing.

FIG. 13 shows that the inlet aperture 24 extends, in a transverse direction, entirely through the probe body 10.

It is understood that the preceeding description is given by way of example only and that various other forms and configurations of the present invention may be provided. For example, the inlet port might be configured in a round arrangement and additional or alternate exhaust ports might be provided.

What is claimed is:

1. A probe for use in sensing temperature and respiration comprising, an elongate housing portion having a rectangular cross-section, said housing having located therein a channel having first and second inlet apertures located in top and bottom surfaces, respectively, of said rectangular cross-section housing, said top and bottom surfaces being on the longer sides of said rectangular cross-section, said channel extending transversely through the entire housing from top to bottom, a tubular rod portion mounted on one end of said elongate housing, said housing and said tubular rod portion being constructed and arranged so as to be symmetrical about their longitudinal axis, temperature sensing means mounted on the end of said tubular rod distal to said housing for insertion into the mouth, respiration sensing means mounted inside said housing and in communication with said channel, wherein one of said first and second inlet apertures is positioned on said housing to be in the path of nasal airflow when said probe is inserted in the mouth.

2. The probe of claim 1 wherein said temperature sensing means and said respiration sensing means each comprise a thermistor.

3. The probe of claim 1 further comprising a conically tapered metallic cap affixed to the end of said tubular rod such that said metallic cap completely covers said temperature sensing means.

4. The probe of claim 1 further comprising at least one exhaust port located substantially towards the rear of said housing and in communication with said channel.

5. The probe of claim 1 wherein said housing portion is provided with a tapered portion in the vicinity of the connection with said tubular rod and wherein a top surface of said housing in said connection vicinity is substantially flat.

6. The probe of claim 5 wherein two exhaust ports are provided located in the narrower sides of said housing and communicating with said channel.

7. The probe of claim 6 further comprising a through passageway for said communication between said channel and said exhaust ports and wherein said respiration means is located within said through passageway.

8. The probe of claim 7 comprising means arranged adjacent to said housing for obstructing one of said first and second inlet apertures of said channel, thereby creating a wind tunnel to force said nasal airflow into said through passageway over said respiration sensing means and out said two exhaust ports.

* * * * *